US006792317B1

(12) United States Patent  
Doan et al.

(10) Patent No.: US 6,792,317 B1
(45) Date of Patent: Sep. 14, 2004

(54) IMPLANTABLE ELECTRIC LEAD AND ELECTRICAL COUPLING

(75) Inventors: Phong D. Doan, Stevenson Ranch, CA (US); Lisa Caffee, Canyon Country, CA (US); Kerwyn Schimke, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 372 days.

(21) Appl. No.: 09/866,041

(22) Filed: May 24, 2001

(51) Int. Cl.[7] .............................................. A61N 1/05
(52) U.S. Cl. ...................................................... 607/122
(58) Field of Search ................................ 607/122, 119, 607/116, 125; 439/909

(56) References Cited

U.S. PATENT DOCUMENTS

| | | | |
|---|---|---|---|
| 5,954,759 A | 9/1999 | Swoyer et al. | 607/122 |
| 6,026,567 A | 2/2000 | Swoyer et al. | 29/854 |
| 6,129,749 A | 10/2000 | Bartig et al. | 607/122 |
| 6,285,910 B1 * | 9/2001 | Verness et al. | 607/122 |

* cited by examiner

Primary Examiner—Angela D. Sykes
Assistant Examiner—Roderick Bradford

(57) ABSTRACT

An electrical lead in which a transitional coil conductor near a proximal end of the lead is electrically connected to a wire conductor distal of the coil conductor. The transitional coil is connected to an electrical connector at the proximal end of the lead. The electrical connector may be a standard ring and pin connector such as an IS-1 standard electrical connector often used in implantable medical devices. A second coil conductor runs substantially the entire length of the lead from its proximal to its distal end. The transitional coil is connected to the wire conductor through a coupling. The coupling includes a channel configured to receive the second coil conductor to allow it to run through the coupling. The coupling further includes a coil receiver configured to receive the distal end of the transitional coil to hold it in electrical contact with the electrically conductive body of the coupling. The coupling also includes a connector sleeve receiver, which receives a connector sleeve that is attached to and in electrical contact with a proximal end of the wire conductor. The wire conductor is thereby held in electrical contact with the connector at the proximal end of the lead through the transitional coil and the coupling. Alternative embodiments may include multiple coil conductors held in electrical contact with multiple wire conductors through multiple couplings.

31 Claims, 3 Drawing Sheets

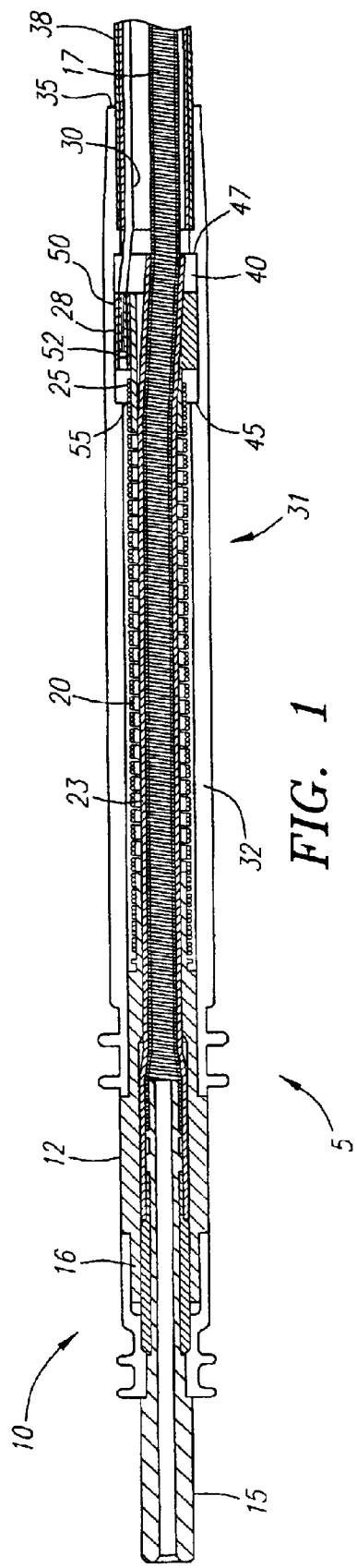
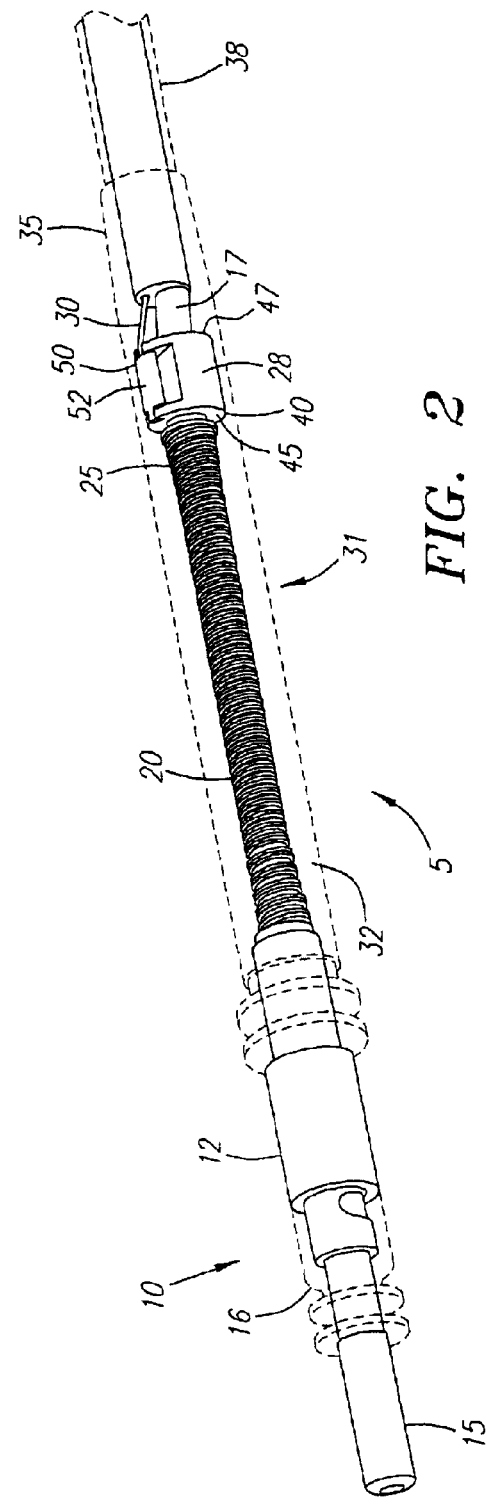

US 6,792,317 B1

IMPLANTABLE ELECTRIC LEAD AND ELECTRICAL COUPLING

FIELD OF THE INVENTION

The invention relates generally to electrical leads used with implantable medical devices, and more particularly, to an implantable electrical lead incorporating a novel, secure, and readily manufactured coupling between electrical conductors inside the lead.

BACKGROUND OF THE INVENTION

Implantable electrical leads are used with implantable medical devices to provide electrical contact between the implantable medical device and a region of a patient's anatomy that is remote from the device.

Cardiac pacemakers include batteries and controllers to deliver regular patterns of electrical signals to the tissues of the heart to help maintain a patient's normal pulse. Because the batteries and controllers must be of considerable size, and because it is generally undesirable to perform highly invasive surgeries on the heart itself, the batteries and controllers are generally implanted in a more accessible region somewhat remote from the heart. A sealed package containing the batteries, processor, and other components of the pacemaker may be implanted, e.g., in a space created in the region of the patients shoulder. This package is then electrically connected to the patient's heart by a thin, flexible electrical lead implanted between the main body unit of the pacemaker and the tissue of the heart. The pacing signals are then delivered to the heart from the main unit over the electrical lead.

Implantable cardiac defibrillators are implantable devices that continuously monitor electrical signals from a patient's beating heart. When the defibrillator detects a predetermined adverse signal pattern, for example, signals indicating cardiac arrhythmia, the defibrillator delivers a strong electrical impulse to reestablish the normal electrical rhythm—and thus a regular pulse—in the patient's heart.

In an implantable cardiac defibrillator, the package containing the batteries, monitor, controller, and the other components of the main body unit may be implanted remotely from the heart, usually again in the region of the patient's shoulder, but sometimes elsewhere. In a device of this type, not only are electrical impulses delivered through the lead, but the controller monitors signals from the heart through the lead as well.

Other devices are known in which electrical signals are delivered between a main unit and region of the body somewhat away from the main unit, and still more such devices will likely be made in the future.

In all such devices that transmit signals or impulses over an implantable lead, it is generally desirable for the lead to be thin and flexible so that the lead can be implanted into the body conveniently and with minimal discomfort and distress. At the same time, the lead must provide a highly reliable and secure connection between the electrical base unit and the target location inside the patient's body. Perhaps less obviously, it is sometimes desirable to design a degree of "pushability" or "torqueability" into certain regions of such leads to facilitate the leads' delivery to their remote destinations inside the body.

Leads have been developed that include helical metal coils as conductors. In some such leads, one relatively thin conductor coil is disposed inside another coil of slightly larger diameter with an insulator layer between them. In other leads, helical conductor coils run parallel to one another along the body of the lead. Such coils have been found reliable and deliverable, and have been widely adopted by medical practitioners.

In some cases, though, leads having coaxial or otherwise parallel helical coils are neither as thin nor as flexible as might be desired. Some attention has been paid, therefore, to potential new leads in which one or more flexible wire conductors might be used in place of one or more of the helical coils of a known lead. Each such flexible wire conductor might be a single strand of wire, or it might include multiple strands of a very thin and highly flexible conductor material, such as in a wrapped wire cable. Such flexible wire conductor leads might then be thinner and provide greater flexibility than known leads, which might be highly advantageous in many applications.

Lead designers know, however, that reliability and failure resistance are key criteria in the performance of these electrical leads. An implantable electrical lead remains intact and functional inside the patient's body for long periods, perhaps many years. At best, lead failure can require a painful and dangerous surgical explantation to replace the failed lead. If the lead fails to deliver a crucial signal at a critical time, the patient may very well die.

It is vital to avoid compromising a lead's robustness and reliability in the quest for flexibility and small size. The lead conductors themselves must obviously provide sufficient strength and failure resistance, including resistance to mechanical fatigue. Connections between components within the lead must also perform satisfactorily.

It would be desirable, therefore, to devise new lead constructions that offer desired combinations of flexibility and thinness in certain regions of the lead, while avoiding any undue impairment of the lead's reliability or performance. The present invention attempts to meet these objectives in a lead that has good performance characteristics and that is readily, reliably, and conveniently manufactured. Representative embodiments of leads incorporating the invention are depicted in the accompanying figures and described in detail below.

SUMMARY OF THE INVENTION

The invention provides electrical leads suitable for implantation in a human patient and electrical couplings for providing secure electrical connections between components in such leads.

A representative embodiment of such a lead includes an electrically conductive connector at a proximal end of the lead. The connector may be a standard connector commonly used with implantable medical devices, or it may be a custom connector. An electrically conductive transitional coil is electrically connected to the electrical connector, with a wire conductor electrically connected by an electrically conductive coupling to the transitional coil. This construction provides a particularly advantageous construction featuring robust and secure electrical connections between the electrical components, with high flexibility provided at the lead's distal end by the wire conductor.

A preferred embodiment of the electrical coupling includes an electrically conductive coupling body. The coupling body in this embodiment includes structure defining a connector sleeve receiver. A corresponding connector sleeve fits over an end of the wire conductor and is attached to the wire conductor to hold it in secure electrical contact with the coupling body. The coupling body also includes a coil receiver configured to receive and hold a distal end of the transitional coil in secure electrical contact with the coupling body. Secure electrical contact is thereby insured between the transitional coil and the wire conductor. Electrical contact is thus ensured between the connector at the proximal end of the lead and an electrode or another electrical element at the lead's distal end.

An alternative lead features multiple coil conductors fixed by multiple couplings to multiple wire conductors in a single lead.

BRIEF DESCRIPTION OF THE DRAWINGS

Representative embodiments of the invention are described in detail below and in conjunction with the appended drawings, in which:

FIG. 1 is a side-section view showing a proximal portion of an electrical lead;

FIG. 2 is a partial phantom view showing internal details of the proximal portion of the electrical lead of FIG. 1;

DESCRIPTION OF THE PREFERRED EMBODIMENTS

Figure 3:
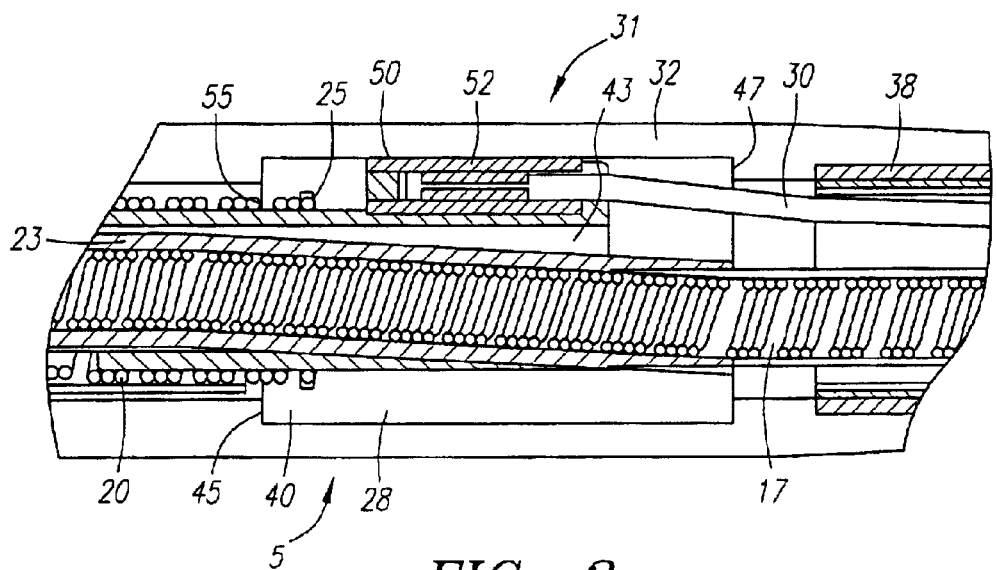
FIG. 3 is a side-section view showing details of an electrical coupling used in the lead of FIG. 1.

FIG. 1 is a side-section view showing a proximal portion of a representative embodiment of an electrical lead 5. The elongate lead has proximal and distal ends, with a connector 10 at the proximal end of the lead. The connector may be a custom connector, but will more commonly be a standard connector specified for use with medical devices. The connector may be, for example, an IS-1 connector, which is a type often used with cardiac pacing leads.

The connector 10 includes two electrically conductive connection components—a connector ring 12 and a connector pin 15. The connector ring 12 and connector pin 15 are electrically isolated from one another by insulative materials 16 in the connector.

The connector pin 15 is in electrical contact with a coil conductor 17, which usually runs substantially the entire length of the lead 5, and which is typically electrically connected to a first electrode (not shown) at the distal end of the lead. The connector pin is usually "electrically connected" or "in electrical contact with" the electrode in the sense that a continuous electrical path exists between the connector pin and the electrode. Other components in the lead are of course "electrically isolated" from one another, meaning that there is an insulative material or an air gap between those two components and there is thus no continuous electrical pathway between them.

The connector ring 12 is fixed in electrical contact with an electrically conductive transitional coil 20, which is disposed around the coil conductor 17. The transitional coil 20 is electrically isolated from the coil conductor 17 by an insulative layer 23 that overlies the coil conductor 17. The transitional coil 20 is considerably shorter than the coil conductor 17. The transitional coil 20 has a distal end 25, which is well proximal of the distal end (not shown) of the lead 5.

An electrically conductive coupling 28 is electrically connected to the distal end 25 of the transitional coil 20. A wire conductor 30 is electrically connected to the conductive coupling, and is thereby electrically connected to the transitional coil. The wire conductor may be for example, a multi-stranded wire cable, or it may be a single strand of wire. The wire conductor is disposed inside an electrically insulative elongate lead body 31. The wire conductor runs inside the lead body generally parallel to the coil conductor 17. The wire conductor runs from the coupling to a location near the distal end (not shown) of the lead 5. The wire conductor will generally connect to a second electrode (not shown) at the distal end of the lead.

In the preferred embodiment, an electrically insulative connector boot 32 is disposed around the transitional coil 20. As shown in FIG. 1, the connector boot has a distal end 35 that is distal of the coupling 28 that joins the wire conductor 30 to the distal end 25 of the transitional coil. A distal lead body member 38 overlies the conductive elements of the lead 5 in the region distal of the connector boot. The connector boot and the distal lead body member cooperate to form the lead body 31. The connector boot provides strain relief and a relatively smooth surface transition between the connector 10 at the proximal end of the lead and the exterior surface of the distal lead body member distal of the connector boot.

FIG. 2 is a partial phantom view showing internal details of the proximal end of the lead 5 illustrated in FIG. 1. Among these details are the electrical connector 10, the transitional coil 20, and the electrically conductive coupling 28 between the wire conductor 30 and the transitional coil.

FIG. 3 is a side section view showing details of the coupling 28 shown in FIG. 1. The coupling includes an electrically conductive coupling body 40. The coupling body includes structure defining a channel 43 through the coupling body. The channel is configured to receive the coil conductor 17, which runs through the channel from a proximal side 45 to a distal side 47 of the coupling body. The insulative layer 23 disposed around the coil conductor isolates the coil conductor electrically from the electrically conductive coupling body.

The coupling 28 also includes structure defining a connector sleeve receiver 50, which includes a region or space in the coupling that is configured to receive an electrically conductive connector sleeve 52. The connector sleeve is configured to receive the proximal end of the wire conductor 30. The connector sleeve is crimped, welded, or otherwise attached to the wire conductor to hold the wire conductor In secure electrical contact with the coupling body 40.

The coupling 28 further includes structure defining a coil receiver 55 on the proximal side 45 of the coupling body 40. In the embodiment shown in FIGS. 1 and 3, the coil receiver is an opening in the proximal side of the coupling body. The distal end 25 of the transitional coil fits inside this opening in secure electrical contact with the electrically conductive coupling body.

Figure 4:
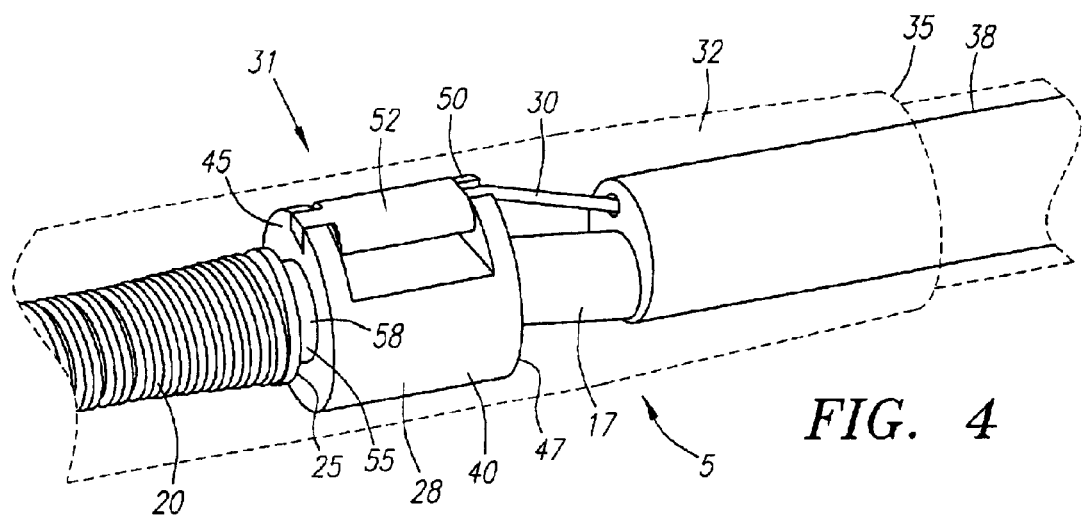
FIG. 4 is a partial phantom view showing details of an electrical coupling used in the lead of FIG. 2.

FIG. 4 is a partial phantom view showing details of the coupling 28 and the components connected to it. In the embodiment depicted in FIG. 4 (and in FIG. 2), the coil receiver 55 is a generally cylindrical body 58 that projects from the coupling body 40. The generally cylindrical body is sized to receive the distal end 25 of the transitional coil 20 in secure electrical contact with the electrically conductive coupling body 40. Among the elements shown in FIG. 4 are the transitional coil 20, the connector sleeve 52, the wire conductor 30, the coil conductor 17 (inside its insulative layer), and the proximal end of the distal lead body member 38. All of these components are shown assembled inside the connector boot 32. The various components of the lead may be secured to one another by welding, crimping, adhesives, or any other suitable means of attachment depending upon the materials of the components and the requirements of the joints between them.

Referring again to FIG. 1, continuous and secure electrical contact is maintained between the connector ring 12 at the proximal end of the lead 5 and the electrode (not shown) at the distal end of the lead. An electrical pathway is provided from the connector ring to the electrode through the transitional coil 20 to the coupling 28, from the coupling through the connector sleeve 52 to the wire conductor 30, through the wire conductor down the lead, and ultimately to the electrode at the lead's distal end. A second, independent electrical pathway exists between the connector pin 15, the coil conductor 17, and, usually, a second electrode near the distal end of the lead.

Figure 5:
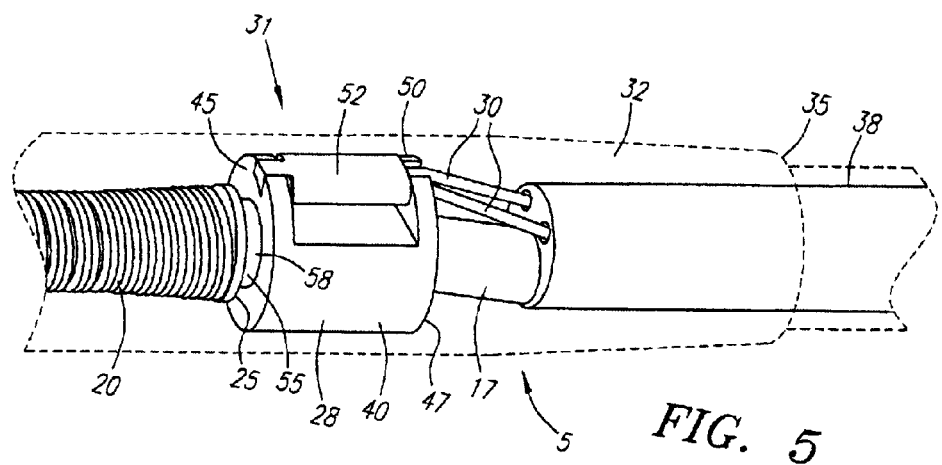
FIG. 5 is a partial phantom view showing internal details of an alternative electrical lead.

The invention can be used in a variety of alternative configurations. For example, FIG. 5 is a partial phantom depiction of an alternative embodiment in which two parallel wire conductors 30 are connected through the connector sleeve 52 to the coupling body 40. Both of these wire conductors are connected to a single connector ring at the proximal end of the lead, and will thereby provide a connection between the connector ring and two or more electrodes at different locations at the distal end of the lead.

Figure 6:
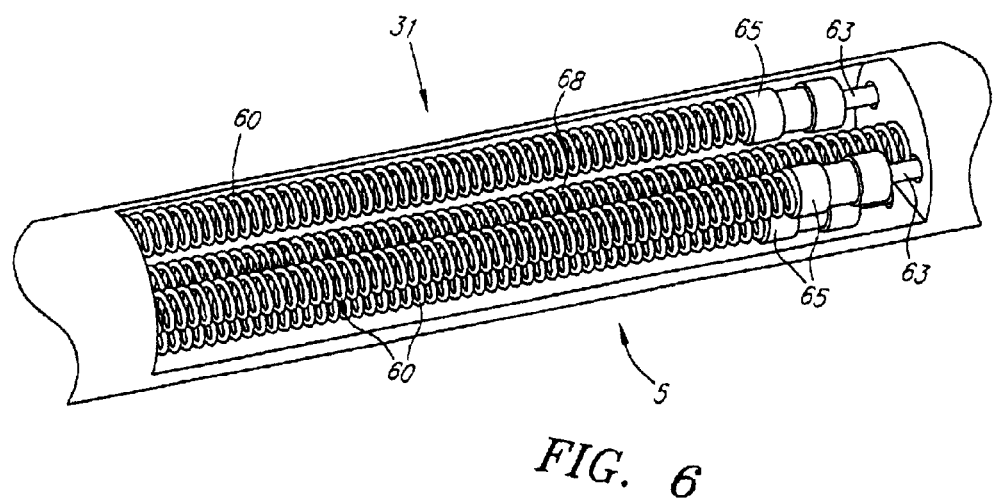
FIG. 6 is a cut-away view of another alternative electrical lead.

Another possible configuration is shown in the phantom view of FIG. 6. In this embodiment, three conductor coils 60 are electrically connected to a corresponding three conductor wires 63 or wire cables through three electrically conductive crimp couplings 65. A fourth central conductor coil 68 lies in the center of the lead between the three outer conductor wires and runs substantially the entire length of the lead in this embodiment. In this embodiment the conductor coils are electrically connected to the crimp couplings, which are crimped in turn onto the conductor wires. An embodiment of this type would generally include insulative materials overlying some or all of the coil conductors to electrically isolate them from one another. These insulative materials are omitted from FIG. 6 for clarity.

Using a transitional coil between a connector at the proximal end of a lead and a wire conductor at the distal end and coupling the transitional coil through a secure coupling to the wire conductor yields a lead that combines high flexibility at the distal end of the lead with reliable and secure electrical connections between the lead components. Some representative embodiments of leads incorporating such constructions are described herein to illustrate the principles of the current invention. Those of skill in the art will no doubt devise numerous and various additions, revisions, and modifications to these representative embodiments. The scope of the invention is not limited to the representative embodiments described herein. The true scope of the invention must instead be determined by reference to the appended claims, along with the full scope of equivalents to which those claims are legally entitled.

What is claimed is:

1. An electrical lead having proximal and distal ends, the lead comprising:
   an electrically conductive connector;
   an electrically conductive transitional coil in electrical contact with the connector and running from the connector toward the distal end of the lead, the transitional coil having a distal portion;
   an elongate wire conductor, the wire conductor having a proximal portion; and
   an electrically conductive coupling establishing electrical contact between the distal portion of the transitional coil and the proximal portion of the wire conductor;
   wherein the conductive coupling is proximal to the wire conductor and distal to the transitional coil.

2. The electrical lead of claim 1, and further comprising an electrically insulative connector boot disposed around the transitional coil, the coupling, and at least a proximal portion of the wire conductor.

3. The electrical lead of claim 2, and further comprising an electrically insulative distal lead body member disposed over at least a portion of the wire conductor and the coil conductor in a region distal of the coupling and the connector boot.

4. The electrical lead of claim 1, wherein the wire conductor is a single wire strand.

5. The electrical lead of claim 1, wherein the wire conductor is a multi-stranded wire cable.

6. The electrical lead of claim 1, and further comprising a coil conductor electrically connected to the connector and running along the lead generally parallel to the transitional coil and the wire conductor.

7. An electrical lead having proximal and distal ends, the lead comprising:
   an electrically conductive connector;
   an electrically conductive transitional coil in electrical contact with the connector and running from the connector toward the distal end of the lead;
   an elongate wire conductor;
   an electrically conductive coupling establishing electrical contact between the transitional coil and the wire conductor; and
   a coil conductor electrically connected to the connector and running along the lead generally parallel to the transitional coil and the wire conductor;
   wherein the coil conductor is disposed inside the transitional coil in a part of the lead.

8. An electrical lead having proximal and distal ends, the lead comprising:
   an electrically conductive connector;
   an electrically conductive transitional coil in electrical contact with the connector and running from the connector toward the distal end of the lead;
   an elongate wire conductor;
   an electrically conductive coupling establishing electrical contact between the transitional coil and the wire conductor; and
   a coil conductor electrically connected to the connector and running along the lead generally parallel to the transitional coil and the wire conductor;
   wherein the coupling includes structure defining a channel and wherein the coil conductor is disposed inside the channel.

9. An electrical lead having proximal and distal ends, the lead comprising:
   an electrically conductive connector;
   an electrically conductive transitional coil in electrical contact with the connector and running from the connector toward the distal end of the lead;
   an elongate wire conductor; and
   an electrically conductive coupling establishing electrical contact between the transitional coil and the wire conductor; and
   a connector sleeve configured to receive an end of the wire conductor;
   wherein the connector sleeve is securable to the wire conductor and configured to secure the wire conductor in electrical contact with the coupling.

10. The electrical lead of claim 9, wherein the coupling includes structure defining a connector sleeve receiver configured to receive the connector sleeve in electrical contact with the coupling.

11. An electrical lead having proximal and distal ends, the lead comprising:
   an electrically conductive connector;
   an electrically conductive transitional coil in electrical contact with the connector and running from the connector toward the distal end of the lead;
   an elongate wire conductor; and
   an electrically conductive coupling establishing electrical contact between the transitional coil and the wire conductor;
   wherein the coupling includes structure defining a coil receiver configured to receive the transitional coil in electrical contact with the coupling.

12. The electrical lead of claim 11, wherein the coil receiver is an opening in the coupling configured to receive an end of the transitional coil in electrical contact with the coupling.

13. The electrical lead of claim 11, wherein the coil receiver is a projection on the coupling, wherein the transitional coil is configured to be received over the projection in electrical contact with the coupling.

14. The electrical lead of claim 13, wherein the projection is a generally cylindrical body on the coupling.

15. An electrical lead having proximal and distal ends, the lead comprising:
   an electrically conductive connector;
   an electrically conductive transitional coil in electrical contact with the connector and running from the connector toward the distal end of the lead;
   an elongate wire conductor;
   an electrically conductive coupling establishing electrical contact between the transitional coil and the wire conductor;
   a connector sleeve configured to receive an end of the wire conductor;
   wherein the connector sleeve is securable to the wire conductor and configured to secure the wire conductor in electrical contact with the coupling; and
   wherein the connector includes first and second electrically conductive connection components that are electrically isolated from one another, and wherein the transitional coil is electrically connected to the first of the two connection components.

16. The electrical lead of claim 15, wherein the two connection components are a connector ring and a connector pin.

17. The electrical lead of claim 16, wherein the connector is an IS-1 standard electrical connector.

18. The electrical lead of claim 15, and further comprising a coil conductor in electrical contact with the second of the two connection components and electrically isolated from the first connection component, the transitional coil, the coupling, and the wire conductor.

19. The electrical lead of claim 18, wherein the two connection components are a connector ring and a connector pin.

20. The electrical lead of claim 19, wherein the transitional coil is in electrical contact with the connector ring and the coil conductor is in electrical contact with the connector pin.

21. The electrical lead of claim 20, wherein the connector is an IS-1 standard electrical connector.

22. The electrical lead of claim 18, and further comprising an electrically insulative connector boot disposed around the transitional coil, the coupling, and at least a proximal portion of the wire conductor.

23. The electrical lead of claim 22, and further comprising an electrically insulative distal lead body member disposed over at least a portion of the wire conductor and the coil conductor in a region distal of the coupling and the connector boot.

24. An implantable electrical lead having proximal and distal ends, the lead comprising:
   a connector at the proximal end of the lead, the connector comprising an electrically conductive connector ring, and an electrically conductive connector pin, wherein the connector ring and the connector pin are electrically isolated from one another;
   a first conductor in electrical contact with the connector pin and running from the connector pin toward the distal end of the lead;
   an electrically conductive transitional coil disposed around the first conductor, wherein the transitional coil is in electrical contact with the connector ring and electrically isolated from the first conductor, wherein the transitional coil has a distal end proximal of a distal end of the first conductor;
   an electrically insulative connector boot disposed around the transitional coil, wherein the connector boot has a distal end distal of the distal end of the transitional coil;
   an elongate wire conductor disposed parallel to the first conductor, the wire conductor having a proximal end proximal of the distal end of the connector boot;
   an electrically conductive coupling between the transitional coil and the wire conductor, wherein the coupling includes structure defining a channel, wherein the first conductor runs through the channel, and wherein the first conductor is electrically isolated from the coupling; and
   an electrically insulative elongate distal lead body member disposed about the wire conductor and the first conductor in a region distal of the distal end of the connector boot.

25. The implantable electrical lead of claim 24, wherein the first conductor is a coil conductor.

26. The implantable electrical lead of claim 24, wherein the coupling includes a connector sleeve that is securable to the wire conductor and configured to secure the wire conductor in electrical contact with the coupling.

27. The implantable electrical lead of claim 26, wherein the coupling includes structure defining a connector sleeve receiver configured to receive the connector sleeve in electrical contact with the coupling.

28. The implantable electrical lead of claim 24, wherein the coupling includes structure defining a coil receiver configured to receive the transitional coil in electrical contact with the coupling.

29. The implantable electrical lead of claim 28, wherein the coil receiver is an opening in the coupling configured to receive an end of the transitional coil in electrical contact with the coupling.

30. The implantable electrical lead of claim 28, wherein the coil receiver is a projection on the coupling, and wherein the transitional coil is configured to be received over the projection in electrical contact with the coupling.

31. The implantable electrical lead of claim 30, wherein the projection is a generally cylindrical body on the coupling.

* * * * *